(12) United States Patent
Anderson et al.

(10) Patent No.: US 7,126,112 B2
(45) Date of Patent: Oct. 24, 2006

(54) COLD ATOM SYSTEM WITH ATOM CHIP WALL

(76) Inventors: Dana Z. Anderson, 4062 Pinon Dr., Boulder, CO (US) 80304; Jakob G. J. Reichel, 59 rue du Montparnasse, 75014 Paris (FR)

(*) Notice: Subject to any disclaimer, the term of this patent is extended or adjusted under 35 U.S.C. 154(b) by 0 days.

(21) Appl. No.: 11/074,888

(22) Filed: Mar. 8, 2005

(65) Prior Publication Data

US 2005/0199871 A1 Sep. 15, 2005

Related U.S. Application Data

(60) Provisional application No. 60/552,319, filed on Mar. 10, 2004.

(51) Int. Cl.
*H01S 1/00* (2006.01)
*H01S 3/00* (2006.01)
*H05H 3/02* (2006.01)

(52) U.S. Cl. ................................. 250/251

(58) Field of Classification Search ............ None
See application file for complete search history.

(56) References Cited

U.S. PATENT DOCUMENTS

| 5,172,554 | A * | 12/1992 | Swift et al. | 62/6 |
| 6,303,928 | B1 * | 10/2001 | Buell et al. | 250/251 |
| 6,476,383 | B1 * | 11/2002 | Esslinger et al. | 250/251 |
| 6,548,809 | B1 * | 4/2003 | Bouyer et al. | 250/251 |
| 6,787,759 | B1 * | 9/2004 | Saffman | 250/251 |
| 2004/0262210 | A1 * | 12/2004 | Westervelt et al. | 210/222 |

* cited by examiner

*Primary Examiner*—Nikita Wells
*Assistant Examiner*—Anthony Quash
(74) *Attorney, Agent, or Firm*—Clifton L. Anderson

(57) ABSTRACT

A compact vacuum chamber gives electric and optical access to a microchip, which is part of the chamber. The main use of the microchip is to confine, cool and manipulate cold atoms (atom chip). The main new feature is that the microchip forms one wall of a vacuum cell. This makes the chamber compact and lightweight, provides large optical access combined with small overall size, eliminates in-vacuum cabling, and makes the back surface of the chip accessible from the outside (e.g., for cooling and/or additional field-producing elements).

7 Claims, 4 Drawing Sheets
(1 of 4 Drawing Sheet(s) Filed in Color)

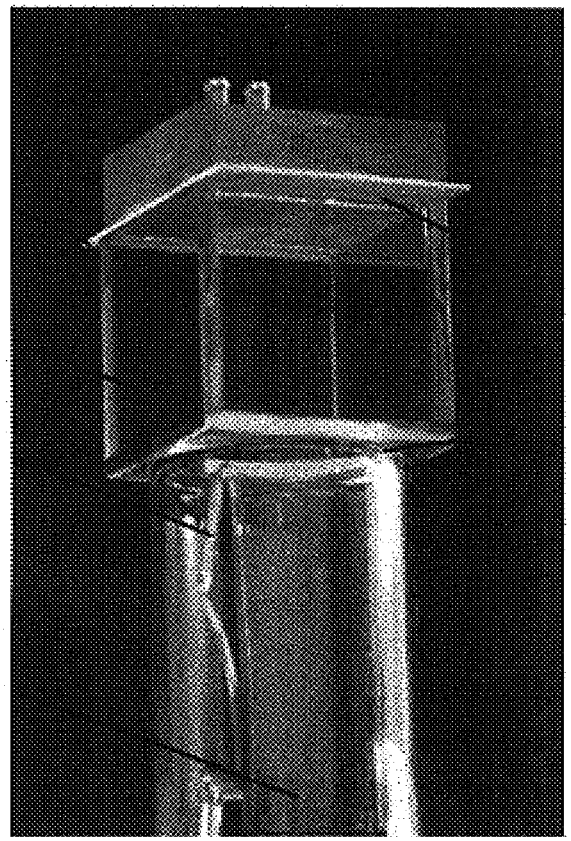
FIG. 3
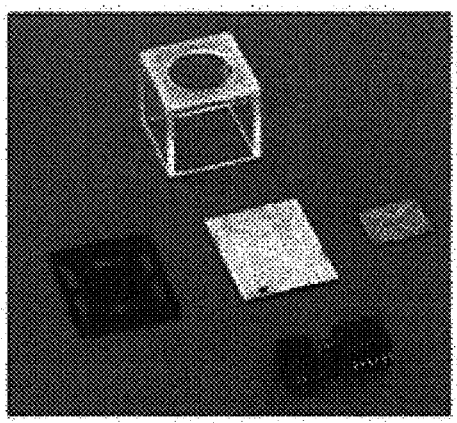 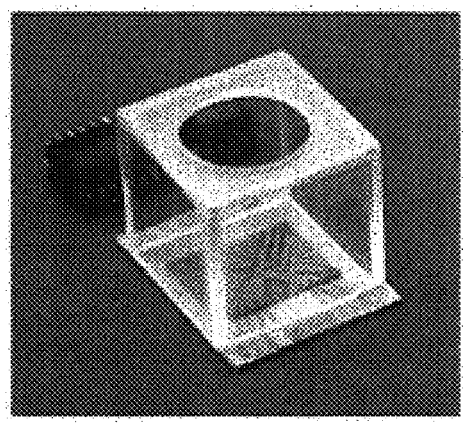
FIG. 4A  FIG. 4B

COLD ATOM SYSTEM WITH ATOM CHIP WALL

This application claims the benefit from the filing data for U.S. Provisional Patent Application No. 60/552,319 filed Mar. 10, 2004. This application is incorporated in its entirety herein by reference.

BACKGROUND OF THE INVENTION

The present invention relates to cold-atom chips and, more particularly, to vacuum cells for sensing and manipulating cold atoms. A major objective of the invention is to provide an improved cold-atom vacuum cell.

Cold atoms and ions are on the way from the research lab to technical applications such as 1) atom interferometry, e.g., used for ultra sensitive sensors (M. A. Kasevich. *Coherence with Atoms*. Science, 298, 1363 (2002)); 2) time and frequency standards; and 3) quantum information processing. All current cold atom and ion applications require an ultrahigh vacuum (UHV) apparatus with optical access. In addition, a multipolar electrical feedthrough is typically required when cold atoms are produced and manipulated with atom chips (J. Reichel, W. Hansel, and T. W. Hansch. *Atomic Micromanipulation with Magnetic Surface Traps*. Phys. Rev. Lett., 83, 3398 (1999); R. Folman, P. Krüger, D. Cassettari, B. Hessmo, T. Maier, and J. Schmiedmayer. *Controlling Cold Atoms using Nanofabricated Surfaces: Atom Chips*, Phys. Rev. Lett., 84, 4749 (2000); R. Folman, P. Krüger, J. Schmiedmayer, J. Denschlag, and C. Henkel. *Microscopic atom optics: From wires to an atom chip*. Adv. At. Mol. Phys., 48, 263 (2002); and J. Reichel. *Microchip traps and Bose-Einstein condensation*. Appl. Phys. B, 74, 469 (2002). More specifically, the vacuum chamber of an atom chip typically provides: 1) an ultrahigh vacuum (base pressure $10^{-7}$ Pa or below at the atom-chip surface; 2) multi-line electrical connections between the microchip and the outside; and 3) optical access (windows) for laser cooling, typically, at least 1 $cm^2$ optical access from several directions.

Today's implementations typically have 10–30 electrical contacts. The typical number of contacts is expected to rise in the future, as it did for microprocessors, increasing the electrical feedthrough requirements. Standard atom chip apparatuses use commercial electrical feedthroughs (CF flanges), and use one of two techniques to give optical access to the chip: 1) custom-made glass cells with special seals; or 2) standard, flange-mounted viewports on a metal chamber.

All existing atom chip implementations use the microchip to create magnetic fields. In one case, electric fields have also been used (P. Krüger, X. Luo, M. W. Klein, A. Brugger, A. Haase, S. Wildermuth, S. Groth, I. Bar-Joseph, R. Folman, and J. Schmiedmayer. *Trapping and Manipulating Neutral Atoms with Electrostatic Fields*. Phys. Rev. Lett., 91, 233201 (2003).) All references cited herein are incorporated by reference herein in their entirety.

Optical atom chips (with integrated optics on the chip) have been proposed, e.g., by G. Birkl, F. B. J. Buchkremer, R. Dumke, and W. Ertmer. *Atom optics with microfabricated optical elements*. Optics Comm., 191, 67 (2001) but not realized. The state of the art has been reviewed extensively by R. Folman, P. Krüger, J. Schmiedmayer, J. Denschlag, and C. Henkel. *Microscopic atom optics: From wires to an atom chip, Adv. Opt. Mol. Phys.* Academic Press, Boston (2002), while magnetic atom chips have been reviewed by J. Reichel, ibid. No commercial atom chip products exist as yet. What is needed is an improved cold-atom cell with good vacuum characteristics as well as sufficient optical and electrical access. Preferably, such a cell would be compact for portable applications.

SUMMARY OF THE INVENTION

The present invention provides a cold-atom cell with a wall including an atom chip that allows external access for generating or detecting fields within the cell. For example, the atom chip can include electrical conductors for carrying currents that generate magnetic fields for manipulating cold atoms. Some or all of the other walls can provide optical access, either by being transparent or by including transparent windows, for laser cooling of the atoms. The microchip can protrude beyond one or more adjacent cell walls to provide the external access to the conductors. Alternatively, access can be had using vias extending through the microchip. The atom chip can provide a surface at which the cold atoms are manipulated and/or sensed; alternatively, the active surface can belong to another structure in communication with the atom chip cell wall.

"Atom chip" encompasses chips: 1) that cool atoms so that they become cold and cool cold atoms so that they become cooler; and/or 2) are used to generate magnetic, electrical and/or optical fields to manipulate cold atoms or molecules; and/or 3) measure such fields to detect cold atoms or molecules. The chip can be any kind of substrate with an electronic and/or optical conductor pattern on it. (It may contain additional features, such as electronic components, lenses, micromechanics etc.). Typically, the atom chip provides electrical feedthroughs from the cell exterior to its interior.

The cold-atom cell of the invention provides for several advantages. Firstly, the cold-atom cell can have a small size and lightweight. With both of the standard techniques, the vacuum chamber is much larger than would be required for the function of the atom chip itself. Sealing the chip to a glass cell dramatically reduces the size.

Secondly, the atom-cell permits large optical access combined with small size. Standard technique 1 also allows large optical access, but at the expense of a bulky seals. This is because the special seals used in these cells, e.g., Helicoflex spring-loaded metal seals, available from Helicoflex, require permanent application of compression on the sealing surface. Standard technique 2, using viewports, does not allow large optical access.

Thirdly, the invention reduces or eliminates the need for in-vacuum cabling. Standard techniques require complicated in-vacuum cabling. The present invention replaces some or all required in-vacuum cabling with on-chip conductive paths that are accessible from outside the cell.

Forth, the invention provides access to the back surface of the atom chip from outside. This enables easy cooling in high-current applications, and allows for additional feedthroughs, in this case, "vias" in microchip terminology. These and other features and advantages of the invention are apparent from the description below with reference to the following drawings.

Finally, because the atoms lie dose to the chip surface, they also lie close to the outside of the vacuum system. That distance can be less than a few millimeters, even less than 1 mm. Thus they can be manipulated and controlled by structures on the backside of the atom chip, or just behind the atom chip. This means that the chip can be imbued with greater functionality. Moreover, having close access to the atoms from outside of the vacuum region simplifies the vacuum system, makes ultra-high vacuum easier to maintain, and typically lowers the size and power consumption of the field-producing elements. These and other features and advantages of the invention are apparent in the description below with reference to the following drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a photograph of an upper portion of the vacuum assembly of FIG. 2.

FIG. 2 is a schematic view of a portion of a vacuum assembly for an atom chip in accordance with the present invention.

FIG. 4A is a photograph of components of a vacuum cell of the vacuum assembly of FIG. 2.

FIG. 4B is a photograph showing the components of FIG. 4A assembled to form a vacuum cell.

DETAILED DESCRIPTION

Figure 1:
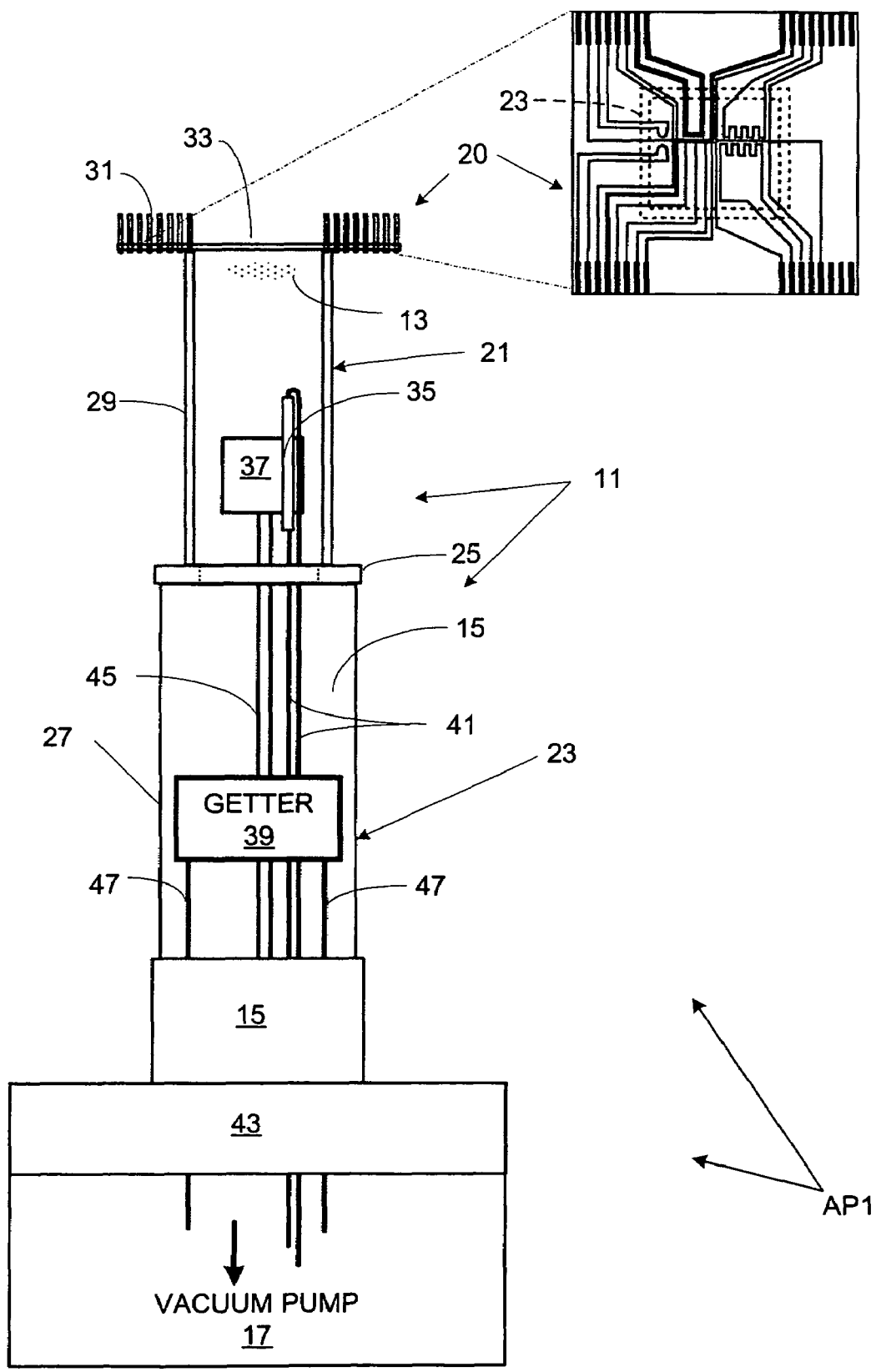
FIG. 1 is a schematic representation of a cold-atom system incorporating a cold-atom cell in accordance with the present invention.

A cold-atom system API, shown schematically in FIG. 1, includes a novel cold-atom cell 11 (with a Bose-Einstein condensate 13 indicated therein), a glass-to-metal interface 15, and a vacuum pump 17. Cell 11 includes an atom chip 20, a dispenser section 21 and a getter section 23, coupled by a disk 25. Getter section 23 has a cylindrical transparent glass wall 27, while disperser section 21 has four rectangular transparent glass side walls 29 defining a square cross section.

Atom chip 20 is patterned to define circuits for controlling and sensing atoms in a Bose-Einstein condensate, as shown in the detail of FIG. 1. Atom chip 20 servers as a top wall for dispenser section 21 and cold-atom cell 11, but extends laterally beyond walls 29, indicated in dash in the detail. This allows leads 31 of atom chip 20 to be positioned laterally from dispenser section 21 of atom cell 20, leaving a central area 33 accessible for on-chip active elements. In addition, the lead-free area 33 allows external field generators and sensors to affect condensate atoms with fields extending through atom chip 20. The leads themselves are connected to electrical elements on the interior side of atom chip 20, which thus serves as an electrical feedthrough between the exterior and interior of cell 11.

As shown in FIG. 1, an alkali metal dispenser 35 and an alkali metal collector 37 are disposed within dispenser section 23, while a getter 39 is disposed within getter section 23. Conductive leads 41 for dispenser 35 extend from dispenser 35 through disc 25, through getter section 23, through interface 15, and through a flange 43 of vacuum 17. Also, a post 45 supporting collector 37 extends through disc 25 to interface 15. In addition, conductive leads 47 for getter 39 extend through interface 15 and flange 43.

Figure 2:
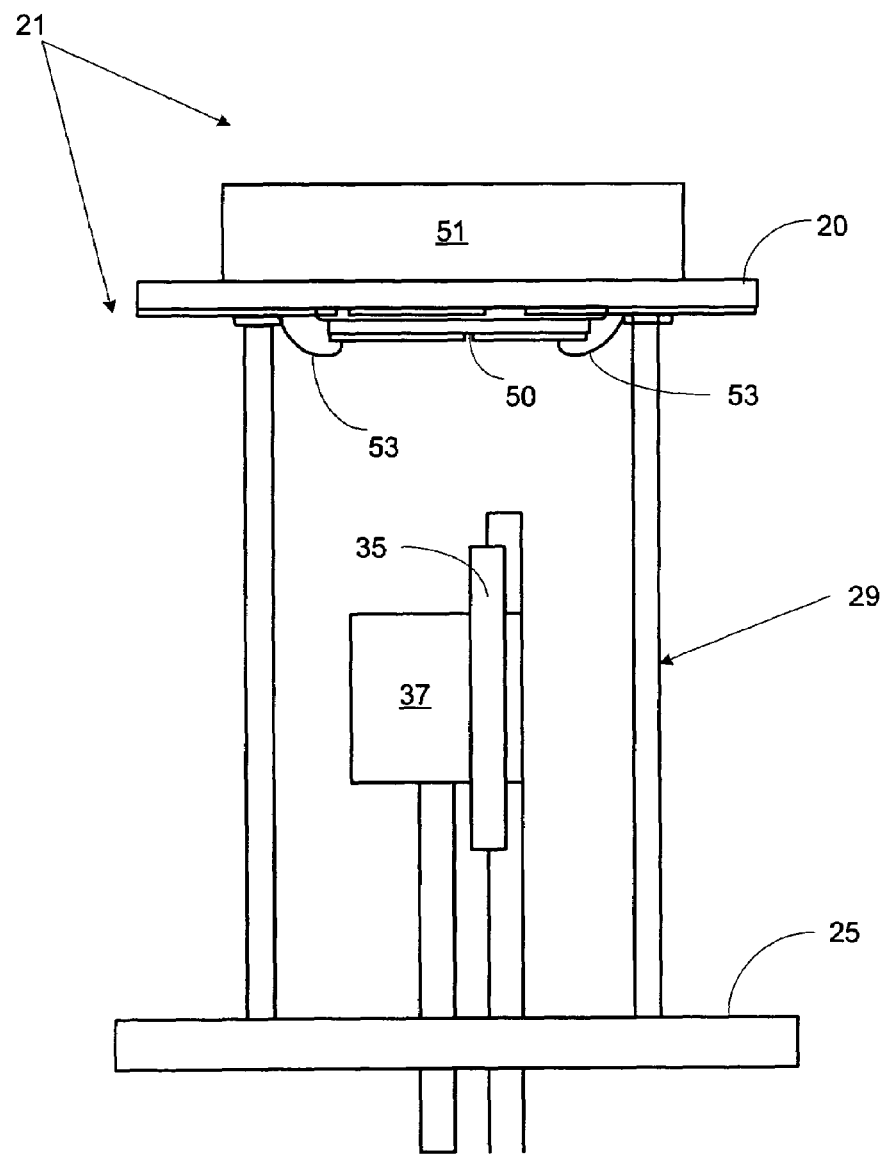
FIG. 2 is a schematic diagram of the cold-atom cell of FIG. 1 modified in that a single atom chip has been replaced by a stacked pair of atom chips.

FIG. 2 shows dispenser section 21 in an alternative setup, with a second atom chip 50 mounted on atom chip 20, and a copper block 51 mounted on the back of atom chip 20. Conductors on chip 50 are electrically coupled to conductors on chip 20 by wire bonds 53.

Tested vacuum chambers in accordance with the present invention have been built in Munich, Germany and in Boulder, Colo. The two realizations are somewhat different but achieve the same functionality. Manufacture starts from an atom chip that has conductors patterned on a substrate. The Munich system uses gold for the conducting material while the Boulder system uses copper. Other conducting material can also be used, such as platinum. The substrate material needs to be vacuum compatible and it is preferable to have high thermal conductivity. Both the Munich and Boulder realizations use aluminum nitride, Examples of other suitable substrates are silicon, sapphire, aluminum oxide, and diamond. The Munich version utilizes a commercially available (e.g., from Hellma-Worldwide, catalog item 704.001), rectangular glass cell for spectroscopy is used. A hole is drilled into the surface that faces the open side (FIG. 3). A commercial glass-to-metal transition (CF flange on one side, open glass tube on the other) is sealed onto the hole. Transitions with 16 mm and 35 mm tube inner diameter have been used. The microchip is sealed on the open side of the cell, with the conductor pattern facing the cell. For both seals, a two-component epoxy glue with low outgassing rate is used (Epo-Tek 353 ND). Other boding techniques can be employed as well. For example, anodic bonding can be used to seal a silicon substrate atom chip to a glass cell, and various other types of glass- or quartz-to-metal seals, or metal-to-metal seals after first applying metal coatings to the substrate and/or cell. The microchip is larger than the cell footprint, allowing for electrical connections. Alternative the chip can be as small as the cell cross section with connections brought to the backside by vias. The CF flange of the glass-to-metal transition is connected to a standard CF cross (35 mm ID), to which a standard ion pump is connected.

The Boulder system is similar except for the use of a fused silica ("quartz") cell instead of glass. Rather than drilling a hole in the end of the quartz cell, the closed end is removed by cutting and the cell end is then lapped smooth. To seal the quartz cell to the glass-to-metal transition a 2.54 cm diameter glass disk is first core-drilled to produce a hole smaller than the inscribed circle of the cell's cross section. This disk is then attached to the glass-to-metal transition and the cell to the upper side of the disk, both using epoxy.

The invention provides for embodiments with and without a heat sink. For example, a copper block can be attached to the backside of the chip to make it more rigid and to remove heat and to make the chip more rigid. On the other hand, omitting the heat sink facilitates access to the back of the chip, which may be patterned. The back pattern can be used to generate electric and magnetic fields that can sense or affect atoms on the inside of the cell. Alternatively, wires can be disposed close to the back of the atom chip to generate the fields.

FIGS. 4A and 4B show crucial elements of the vacuum chamber. The left image (FIG. 4A) shows the individual components, the right image shows (FIG. 4B) how they are assembled. Elements visible in the left image: Back: glass cell, hole has been drilled; center, left to right: photo mask for chip fabrication (not part of the final assembly), base microchip, smaller microchip (see below for role of second chip); front: electrical connector plug. Additional pumping is provided by a Titanium sublimation pump.

The cells built as described above have been baked at temperatures around 100° C. for several days. The Boulder design has been baked at around 170° C. The higher baking temperature corresponds to a greater rate for removing water, making it easier to establish a high vacuum. After baking, a pressure gauge connected to the CF cross indicated a pressure in the lower $10^{-8}$ Pa range.

The thermal expansion coefficients are sufficiently matched to maintain cell integrity. Indeed, the elasticity of the epoxy glue can be sufficient to compensate the difference in expansion coefficients of glass and stainless steel, without a glass-to-metal transition piece. For this test, a Hellma cell (Type 704.002 or similar) was glued directly onto a 35CF flange with a hole for pumping. The glue was Epo-Tek H77. The cell was successfully evacuated, and successfully heated to 80–100° C. While cooling down, however, a crack developed; after venting the cell, it completely broke off the flange.

This shows that expansion matching is beneficial. Two standard microelectronics ceramics, AlN and $Al_2O_3$, have expansion coefficients that are close to those of optical glasses (e.g., BK7, Pyrex). In one of the successful Munich prototypes, AlN ceramics ($\alpha \approx 5 \times 10^{-6}$ $K^{-1}$ was glued to cells made from Schott crown glass B270 ($\alpha \approx 9 \times 10^{-6}$ $K^{-1}$. A still better match would be given for $Al_2O_3$ ceramics and BK7 glass (both have $\alpha \approx 8 \times 10^{-6}$ $K^{-1}$). The expansion coefficient of the glue, Epo-Tek 353ND, is much higher: $\alpha \approx 54 \times 10^{-6}$ $K^{-1}$. However, even such a large mismatch can be tolerated in some cases.

In a demonstration of its utility, an atom-chip cell in accordance with the invention has been used to produce a $^{87}Rb$ Bose-Einstein condensate (BEC) The resulting vacuum system made as described above is a significant reduction in the size and complexity of current BEC systems. All cooling and trapping processes happen from 2 mm to 70 μm below the room temperature chip surface. A BEC of about 1,000 $^{87}Rb$ atoms in $F=2$, $M_F=2$ is achieved after 4.21 seconds of RF forced evaporation. A micro-trap lifetime of 3 to 4 seconds indicates the vacuum near the chip surface is about $10^{-9}$ torr.

Bose-Einstein condensation (BEC) of a dilute atomic vapor is commonly viewed as the atomic analog of the optical laser. Since the first Bose-Einstein condensation in a neutral atom gas in 1995 (M. Anderson, J. Ensher, M. Mattews, C. Wieman, and E. Cornell, Science 269, 198 (1995); K. Davis, M. Mewes, M. Andrews, N. J. van Druten, D. Durfee, D. Kurn, and W. Ketterle, Phys. Rev. Lett. 75, 3969(1995).), it seemed likely that practical applications for condensates could be realized. However the implementation of "atom lasers" is in much the same state as the first generations of optical lasers in the 1950's and 60's. Cold atom guiding and manipulation using lithographically patterned wires on substrates have demonstrated the possibility of making small-scale devices for atom manipulation (D. Müller, D. Z. Anderson, R. J. Grow, P. D. D. Schwindt, and E. A. Cornell, Phys. Rev. Lett., 83, 5194(1999); N. H. Dekker, C. S. Lee, V. Lorent, J. H. Thywissen, S. P. Smith, M. Drndic, R. M. Westervelt, and M. Prentiss, Phys. Rev. Lett., 84, 1124(2000); D. Müller, et al. Opt. Lett. 25, 1382(2000); D. Cassettari, B. Hessmo, R. Folman, T. Maier, and J. Schmiedmayer, Phys. Rev. Lett. 85, 5483(2000).).

Indeed the term "atom chip" connotes a picture of microscale atom-optical devices, perhaps integrated with optics and electronics on a single substrate. The realization of chip based BEC in 2001 (W. Hansel, P. Hommelhoff, T. Hansch, and J. Reichel, Nature 413, 498(2001); H. Ott, J. Fortagh, G. Schlotterbeck, A. Grossmann, and C. Zimmermann, Phys. Rev. Lett. 87, 230401(2001). It was a scientific and technical milestone towards chip-scale coherent atom devices. However, like all BEC systems, chip-scale atomic systems still require an unwieldy assembly of electronic, optical, and vacuum instrumentation. This work reports on the significant simplification of the vacuum system for BEC atom chip production.

Figure 5:
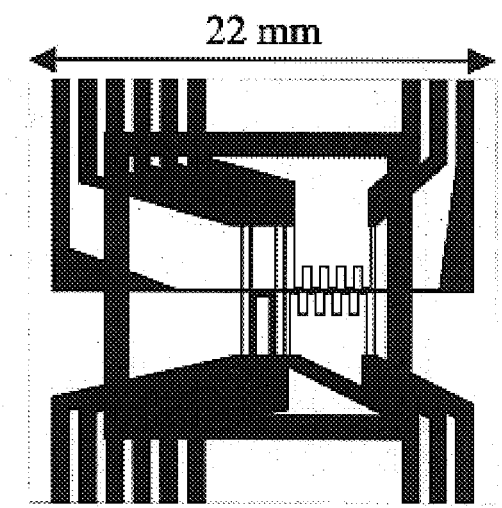
FIG. 5 is a schematic view of a conductor pattern of an atom chip of the assembly of FIG. 2.
Figure 6:
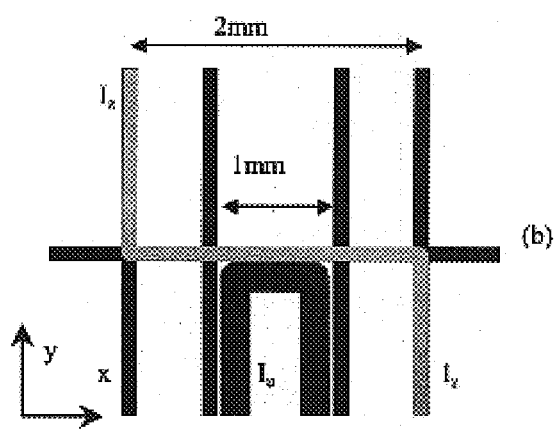
FIG. 6 is a schematic center detail of the conductor pattern of FIG. 5.
Figure 7:
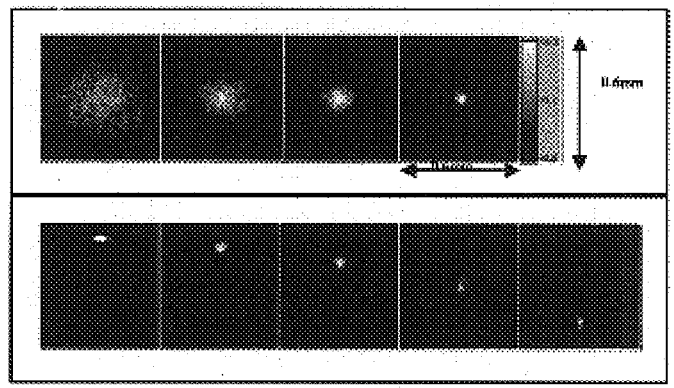
FIG. 7 is a series of photographs demonstrating Bose-Einstein Condensation in atom-cell vacuum system.

The atom chip and its wire pattern are illustrated in FIG. 5 and FIG. 6. FIG. 5 provides a view of the whole chip pattern. The hatched square indicates the position on the quartz cell. FIG. 7 shows a center detail of wires where the BEC is obtained. The U wire ($I_u$, 200 μm wide) is used to create chip MOT, and the Z wire (shown in grey, $I_z$, 100 μm wide) to create IP type magnetic trap by applying a y-directional bias field. The other wires seen in FIG. 6A are not used in this experiment.

The conductor pattern on the atom chip, shown in FIGS. 5 and 6, is made using standard lithographic and electroplating techniques (D. Müller, D. Z. Anderson, R. J. Grow, P. D. D. Schwindt, and E. A. Cornell, Phys. Rev. Lett., 83, 5194(1999); N. H. Dekker, C. S. Lee, V. Lorent, J. H. Thywissen, S. P. Smith, M. Drndic, R. M. Westervelt, and M. Prentiss, Phys. Rev. Lett., 84, 1124(2000); D. Müller, et al. Opt. Lett. 25, 1382(2000); D. Cassettari, B. Hessmo, R. Folman, T. Maier, and J. Schmiedmayer, Phys. Rev. Lett. 85, 5483(2000), J. Reichel, W. Hansel, P. Hommellhoff, and T. W. Hansch, Appl. Phys. B 72, 81(2001).

When augmented with an external y-directional bias field, the "U" shaped wire creates a 3-dimensional quadrupole field and the "Z" shaped wire results in an Ioffe-Pritchard type trap with a nonzero minimum. (For a comprehensive review on chip microtraps, see J. Reichel, W. hansel, P. Hommellhoff, and T. W. Hansch, Appl. Phys. B 72, 81(2001); R. Folman, P. Kruger, J. Denschlag, C. Henkel, and J. Schmiedmayer, Adv. At., Mol. Opt. Phys. 48, 263 (2002); J. Reichel, Appl. Phys. B 75, 469(2002). The 100 μm and 200 μm wide copper wires can support continuous currents up to 4 and 5A respectively for more than 5 minutes.

Following Reichel et al (Ibid), a silver mirror is transferred to the chip surface. After mirror transfer, the chip is assembled with a quartz cell of inner cross section as described above.

Light induced atomic desorption (LIAD) can be employed to achieve large atom number in the MOT and to meet the UHV requirements of Bose-Einstein condensation. (B. P. Anderson and M. A. Kasevich, Phys. Rev. A 63, 023404 (2001); E. B. Alexandrov, M. V. Balabas, D. Budkler, D. English, D. F. Kimball, C.-H. Li, and V. V. Yashchuk, Phys. Rev. A 66, 042903 (2002); S. N. Autov, R. Calabrese, V. Guidi, B. Mai, A. G. Rudavets, E. Scansani, L. ilTomassetti, V. Biancalana, A. Burchianti, C. Marinelli, E. Mariotti, L. Moi, and S. Veronesi, Phys. Rev. A 67, 053401 (2003)] of rubidium from the surfaces of the cell using two UV lamps.

The illustrated embodiment provides for mirror MOT lifetime measurement as an indication of the pressure in the cell. The lifetime is measured by turning off the UV lamps and fitting the decaying MOT florescence to an exponential. Typical measured lifetimes are on the order of 30 s. The MOT lifetime is not determined by the Rb pressure decay after the LIAD loading by noting the number loaded into the MOT after introducing a delay between when the UV lamps are switch off and when the MOT fields are turned on. The Rb partial pressure in the cell decays very rapidly compared to the MOT lifetime; and thus the MOT lifetime is determined by the background pressure in the cell. The MOT lifetime, however, does not directly correlate to the total vacuum pressure, so the micro-trap lifetime of 3 to 4 s can be used to determine the pressure near the chip surface is about $10^{-7}$ Pa.

A mirror-MOT can be used as described by J. Reichel, W. Hansel, and T. W. Hansch, Phys. Rev. Lett. 83, 3398(1999) for the first stage of cooling and trapping. The powers of cooling and re-pumping beams are 30 mW and 6 mW respectively, with beam diameter of 8 mm. The MOT is loaded by applying LIAD for three seconds to increase the rubidium vapor pressure followed by a five second holding time to improve the pressure in the cell. The MOT loaded in this way typically traps about $6\sim7\times10^6$ $^{87}$Rb atoms with a temperature of 200° K, 2 mm away from the surface. The atoms then undergo a compressed MOT (CMOT): the cooling laser red detuning jumps from 10 MHz to 50 MHz and re-pumping power reduces from 6 mW to 100 µW, followed by ramping the quadrupole field gradient from 14 G/cm to 21 G/cm in 20 m/s. At the same time by adjusting bias fields, the atoms are moved toward the surface where the quadruple field is replaced with the field generated by the U wire ($I_U=2A$ and $B_{ybias}=1$ G). After 8 ms in the U wire chip CMOT the atoms have a temperature of 100 µK. 1.7 ms of polarization gradient cooling can be applied by increasing cooling laser red detuning to 70 MHz and switching off all magnetic fields. This further cools atoms to 20 µK. No substantial atom loss is observed during the MOT transfer and cooling steps.

After cooling and trapping, the atoms can be optically pumped into the F=2, $m_F=2$ state in preparation for loading into the Z-trap. About $2\sim3\times10^6$ atoms are loaded into the Z-trap by switching $I_z=4$ A and $B_y=14G$ within 1 ms. Immediately after the loading, the (x,y,z) bias fields ramp from (0,14,0) gauss to (−4, 60,0) gauss within 100 ms. After compression, an RF field is applied to start forced evaporation. At the same time, the trap is further compressed by reducing $I_z$ from 4A to 2.75 A in 2 s. The final trap position is 82 µm away from the surface with trap frequencies of (23, 3600, 3600) Hz. RF evaporation takes place through four logarithmic sweeps. The first RF sweep starts from 45 MHz to 13 MHz for 2.46 s. It is then followed by a 1 s sweep from 13 MHz to 5 MHz, a 500 ms sweep from 5 MHz to 3.5 MHz, and a final 250 ms sweep from 3.5 MHz to 2.85 MHz. At the end of the final sweep, we see a phase transition happen and a Bose-Einstein condensate of 1,000 $^{87}$Rb atoms with a transition temperature of about 300 nK FIG. 7A. As shown in FIG. 7B, the non-isotropic shape during 9 ms TOF (time of flight) is a clear signature of a Bose-Einstein condensate.

The Bose-Einstein Condensation is observed. (a) Absorption images are taken after a 5 ms TOF with different final RF frequencies. From left to right: (1) ν=3.5 MHz, N=42×$10^3$, T=4.4 µk, $<\rho>\approx6\times10^{-4}$; (2) ν=3.0 MHz, N=20×$10^3$, T=1.4 µk, $<\rho>\approx7\times10^{-3}$; (3) ν=2.9 MHz, N=10×$10^3$, T=515 nk, $<\rho>=10^{-1}$; (4) ν=2.85 MHz, N=3×$10^3$, T=230 nk, $<\rho>\approx10$. (b) TOF images of BEC cloud after release with final RF frequency 2.85 MHz. From left to right: TOF (1) 1 ms, (2) 3 ms, (3) 5 ms, (4) 7 ms, and (5) 9 ms. The non-isotropic shape during TOF is a key signature of BEC.

No number loss due to 3-body recombination is observed. A 4 µK/s heating rate that is independent of density leads to 100 ms BEC lifetime. Lowering the trap frequencies by changing Z wire current from 2.75 A to 0.65A, and y bias field from 60 Gauss to 14.5 Gauss, reduces the heating rate to 0.5 µK/s, which corresponds to a BEC lifetime of 300 ms.

In summary, the present invention provides for Bose-Einstein condensations in a small vacuum system. The simple vacuum system and pin connectors dramatically reduce the cost and complexity in building a BEC atom chip system. The achievement of Bose-Einstein condensation in such a system opens a wide range of possible application of integrated on-chip atom optics.

In the foregoing embodiment, care must be taken so that the seal between cell and chip does not impair optical access close to the chip. In an alternative embodiment, shown in FIG. 2, a second, smaller chip may be mounted on the base chip, so that the new chip surface level does not coincide with the seal level. Electrical connection between both chips can be done by wire bonding. In another alternative embodiment, electrical connection to the chip on the air side can be done by various methods, including commercial connectors that are intended for printed circuit board connections (e.g., PCI bus connector).

The invention provides for a variety of configurations in which an atom chip or an assembly of atom chips encloses a vacuum chamber. Herein an atom chip is any generally planar device with elements for interacting with cold atoms, e.g., for cooling, detecting, or manipulating cold atoms. A cold atom herein is an atom, ion, or molecule with a temperature below 1 degree Kelvin. A boundary wall is a wall that, when a vacuum is induced in the interior of a chamber, faces the vacuum on one side an external environment on an opposing side. A boundary wall is at least partially constituted by an atom chip if removing the atom chip would destroy the vacuum capability of the chamber

What is claimed is:

1. A cold atom system comprising a vacuum chamber defining interior and exterior volumes, said chamber having a set of boundary walls for physically separating said volumes, said set including a first boundary wall at least partially constituted by an atom chip, said set including a second boundary wall attached to said first boundary wall.

2. A cold atom system as recited in claim 1 wherein said atom chip extends into said exterior volume so as to overhang said second boundary wall.

3. A cold-atom system as recited in claim 2 wherein said cross section is square or circular.

4. A cold-atom system as recited in claim 1 further comprising an alkali metal dispenser within an interior of said chamber.

5. A cold-atom system as recited in claim 1 further comprising a vacuum pump.

6. A cold-atom system as recited in claim 1 wherein said chamber has an optically transmissive wall.

7. A cold-atom system as recited in claim 1 wherein said atom chip includes electrically conductive paths so that it serves an electrical feedthrough between an exterior and an interior of said chamber.

* * * * *